United States Patent
Wang et al.

Patent Number: 6,104,485
Date of Patent: Aug. 15, 2000

[54] METHOD AND APPARATUS FOR OPTICAL MEASUREMENT OF VERY SMALL FLUID SAMPLES

[75] Inventors: Rong Wang, Sarasota; Harry Fein, Nokomis, both of Fla.

[73] Assignee: World Precision Instruments, Inc., Sarasota, Fla.

[21] Appl. No.: 09/167,753

[22] Filed: Oct. 7, 1998

[51] Int. Cl.[7] .................................................. G01N 1/10
[52] U.S. Cl. .................. 356/246; 356/440; 422/82.09
[58] Field of Search ................... 356/246, 440, 356/417, 125, 12, 13; 422/82.05, 82.09

[56] References Cited

U.S. PATENT DOCUMENTS

| | | | |
|---|---|---|---|
| 4,488,814 | 12/1984 | Johnson | 356/417 |
| 4,989,974 | 2/1991 | Anton et al. | 356/246 |
| 5,416,879 | 5/1995 | Liu | 385/12 |
| 5,444,807 | 8/1995 | Liu | 385/125 |
| 5,570,447 | 10/1996 | Liu | 385/125 |
| 5,604,587 | 2/1997 | Chi et al. | 354/246 |
| 5,736,410 | 4/1998 | Zarling et al. | 422/82.05 |

OTHER PUBLICATIONS

A Cylindrical Liquid–Core–Wave Guide, P. Dress, H. Franke A Fiber–Optic Pipette For Rapid Long–Pathlength Capillary Spectroscopy, C. M. Stellman et al.

*Primary Examiner*—Frank G. Font
*Assistant Examiner*—Zandra V. Smith
*Attorney, Agent, or Firm*—Alix, Yale & Ristas, LLP

[57] ABSTRACT

Fluid samples of very small but precisely equal volume are repetitively collected and subsequently analyzed by being illuminated with measurement light. The collection cells fill spontaneously and the analysis is performed with the sample in the cell.

24 Claims, 6 Drawing Sheets

METHOD AND APPARATUS FOR OPTICAL MEASUREMENT OF VERY SMALL FLUID SAMPLES

BACKGROUND OF THE INVENTION

1. Field of the Invention

The present invention relates to the acquisition of very small liquid samples of precisely identical volume and, particularly, to optically analyzing such minute samples. This invention is also directed to sampling apparatus for repetitively acquiring very small liquid samples of the same volume and, especially, to sampling devices in which an optical measurement may be performed. Accordingly, the general objects of the present invention are to provide novel and improved methods and apparatus of such character.

2. Description of the Prior Art

There are many use environments, the fields of medical research and pharmaceutical development being examples, where it is necessary to accurately acquire fluid samples with volumes which may be as small as a few nanoliters. In these same fields, it is also often desired to measure optical characteristics of the acquired fluid samples. Such optical characteristics may, again by way of example, comprise light absorption, fluorescence or Raman spectra.

It has, in the prior art, been difficult to repetitively acquire very small fluid samples of identical volume and subsequently deliver such samples, without loss, into position for analysis. This difficulty may, to a large degree, be attributed to the fact that the prior art procedures have involved at least one transfer step. Thus, by way of example, it has previously been necessary to "hand-off" the collected sample from the sampling device to the analysis instrument. Additionally, the nature of the previously available sampling devices has rendered it difficult to ensure that each of a plurality of repetitively collected samples would be of identical volume, i.e., the prior art has typically required performance of a quantitative measurement on the collected samples, and this, in turn, has imposed a relatively high tolerance range on the collected sample volume.

SUMMARY OF THE INVENTION

The present invention overcomes the above-briefly discussed and other deficiencies and disadvantages of the prior art and, in so doing, allows very small volume fluid samples to be accurately and repetitively acquired. The samples acquired employing the invention have volumes which may be as small as a few nanoliters. The present invention also enables the acquired fluid samples to be subjected to optical measurement in situ, i.e., without the need for transfer of the sample into another analysis cell. Apparatus in accordance with the invention includes specially constructed capillary tubes, i.e., micro-capillaries. Fluid samples are caused to flow into these small capillary tubes by the natural force of capillary action. The length of these micro-capillaries, and thus the volume thereof, determines sample volume. Restated, capillary tube length is selected such that the bore of the capillary will be completely filled by the liquid being sampled solely due to capillarity, i.e., the sampling device will spontaneously fill until the fluid being sampled reaches the distal end of the micro-capillary. Accordingly, the specially constructed capillary tubes of the invention may be employed to repetitively collect samples of identical volume.

The capillary tube sampling devices of the present invention also possess the ability to function as liquid core optical waveguides. These specially constructed capillary tubes preferably comprise a rigid, transparent capillary tube having an external coating of a material characterized by a refractive index which is less than that of water. A liquid sample filling the core region of the waveguide may be illuminated in situ by measurement light. Light resulting from the passage of measurement light through the sample will contain information of interest relative to the sample. This information may be ascertained by capture and subsequent analysis of the information containing light.

Sampling apparatus in accordance with a preferred embodiment of the invention includes, in addition to the above-discussed specially constructed micro-capillary/optical waveguide, a tubular holder. A first, i.e., the distal, end of the capillary tube is engaged by a first end of the holder and the capillary bore is open to, i.e., is in direct fluid communication with, the interior of the holder which, in turn, must be at atmospheric pressure when the waveguide is to be filled. The capillary tube extends from the holder for insertion of the proximal end thereof into a fluid to be sampled. A collected sample may be expelled from the capillary tube by pressurization of the interior of the holder. The holder, also in accordance with the preferred embodiment of the invention, supports an optical fiber which is, at least in the region thereof located in proximity to the first end of the capillary tube, in axial alignment with the capillary tube. Measurement light may be launched into the capillary tube from this optical fiber and/or light may be received from the capillary tube and transmitted to an analysis instrument via this optical fiber.

Also in accordance with a preferred embodiment of the invention, the holder mates with an enclosure in which measurement light which has been transmitted through the sample or light emitted by the sample is collected and, in some cases, analyzed. When the enclosure and holder are so mated, the micro-capillary sampling tube/optical waveguide will be located within the enclosure and thus shielded from ambient light. Such shielding can enhance the efficiency of collection of the information containing light for subsequent analysis.

BRIEF DESCRIPTION OF THE DRAWINGS

The present invention may be better understood, and its numerous objects and advantages will become apparent to those skilled in the art, by reference to the accompanying drawings wherein like reference numerals refer to like elements in the several figures and in which.

DESCRIPTION OF THE DISCLOSED EMBODIMENTS

Figure 1:
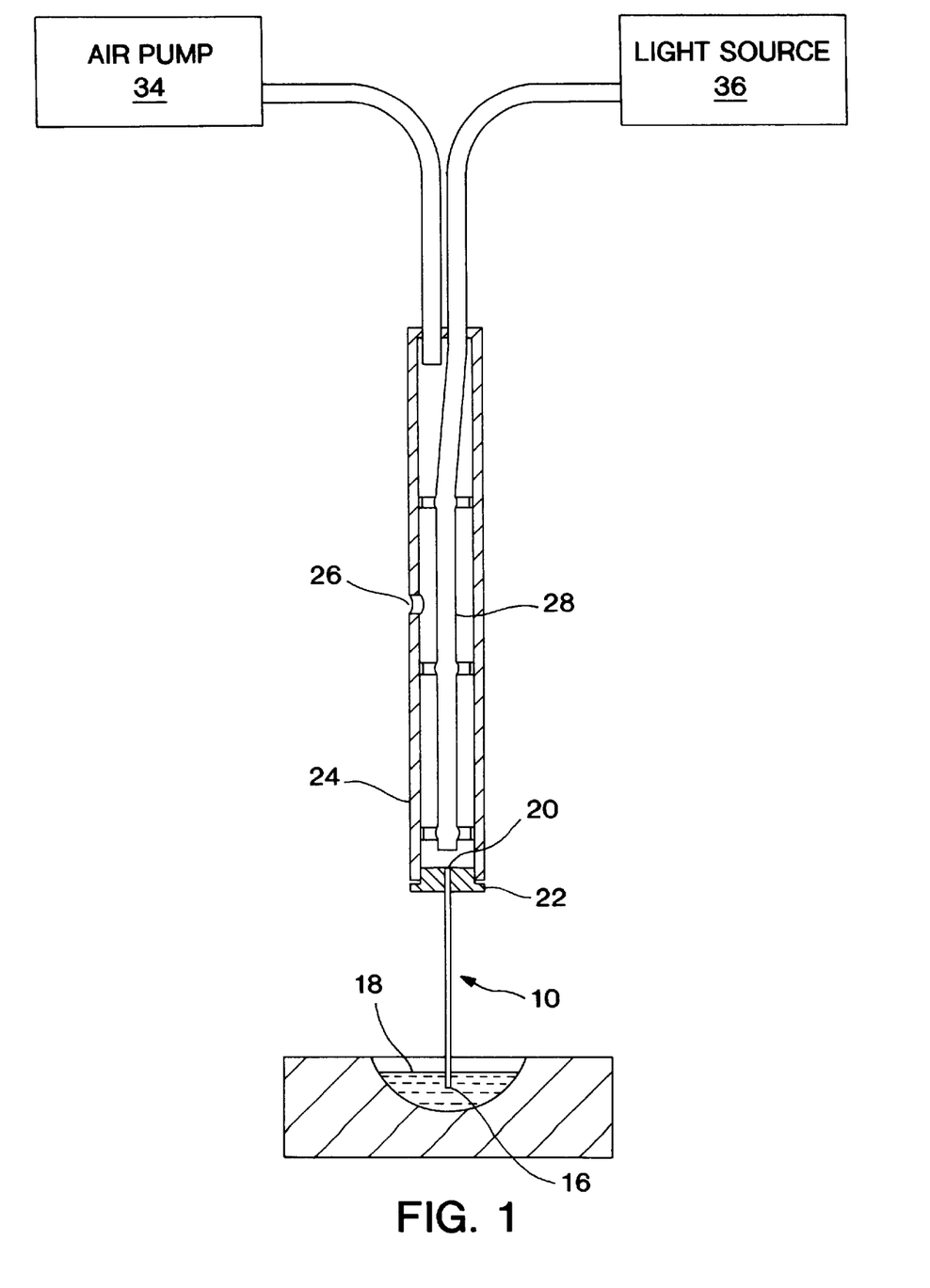
FIG. 1 is a schematic, side-elevational view, partly in section, depicting a first embodiment of sampling apparatus in accordance with the invention.
Figure 2:
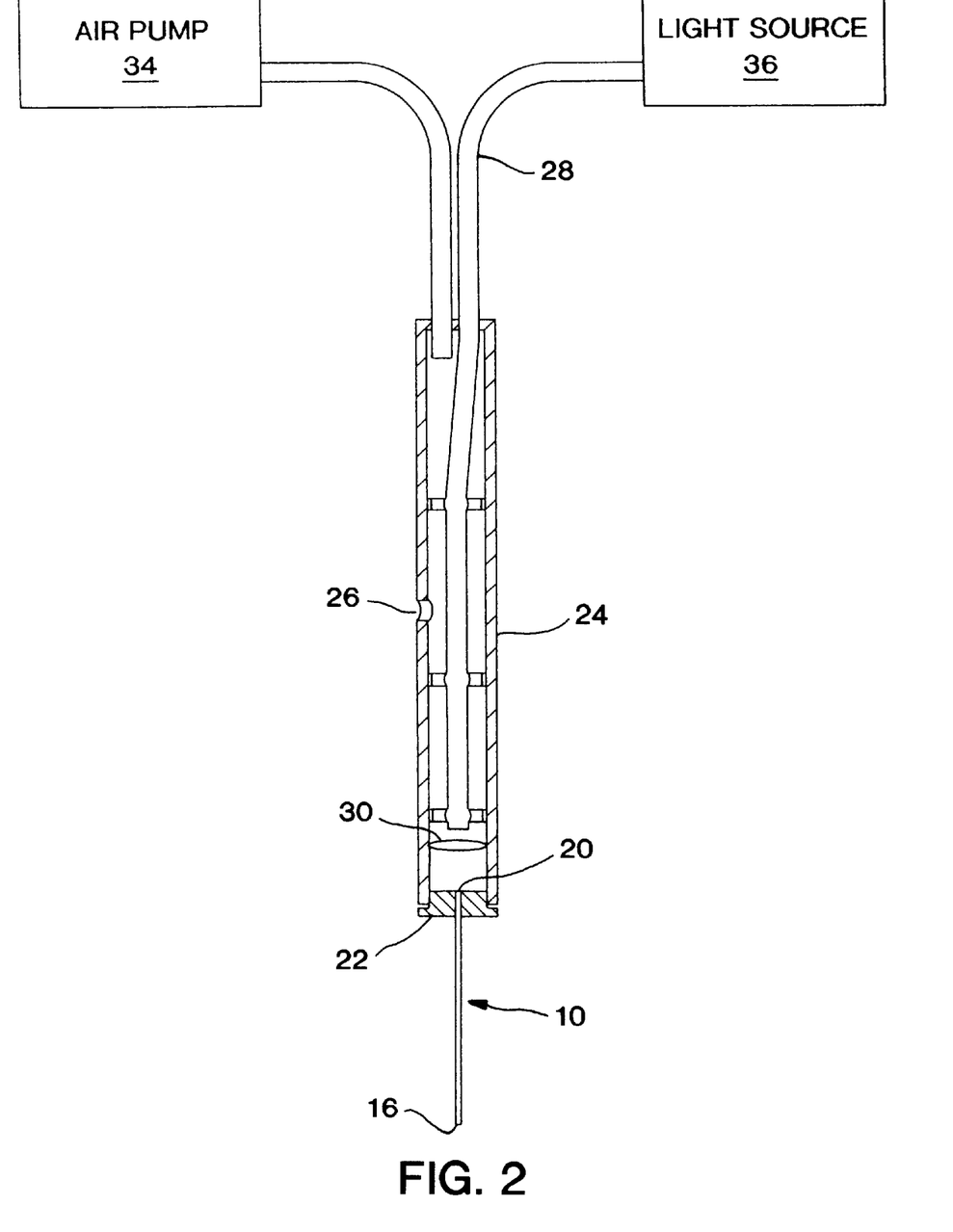
FIG. 2 is a view similar to FIG. 1 depicting a second embodiment of sampling apparatus in accordance with the invention.
Figures 3A, 3B:
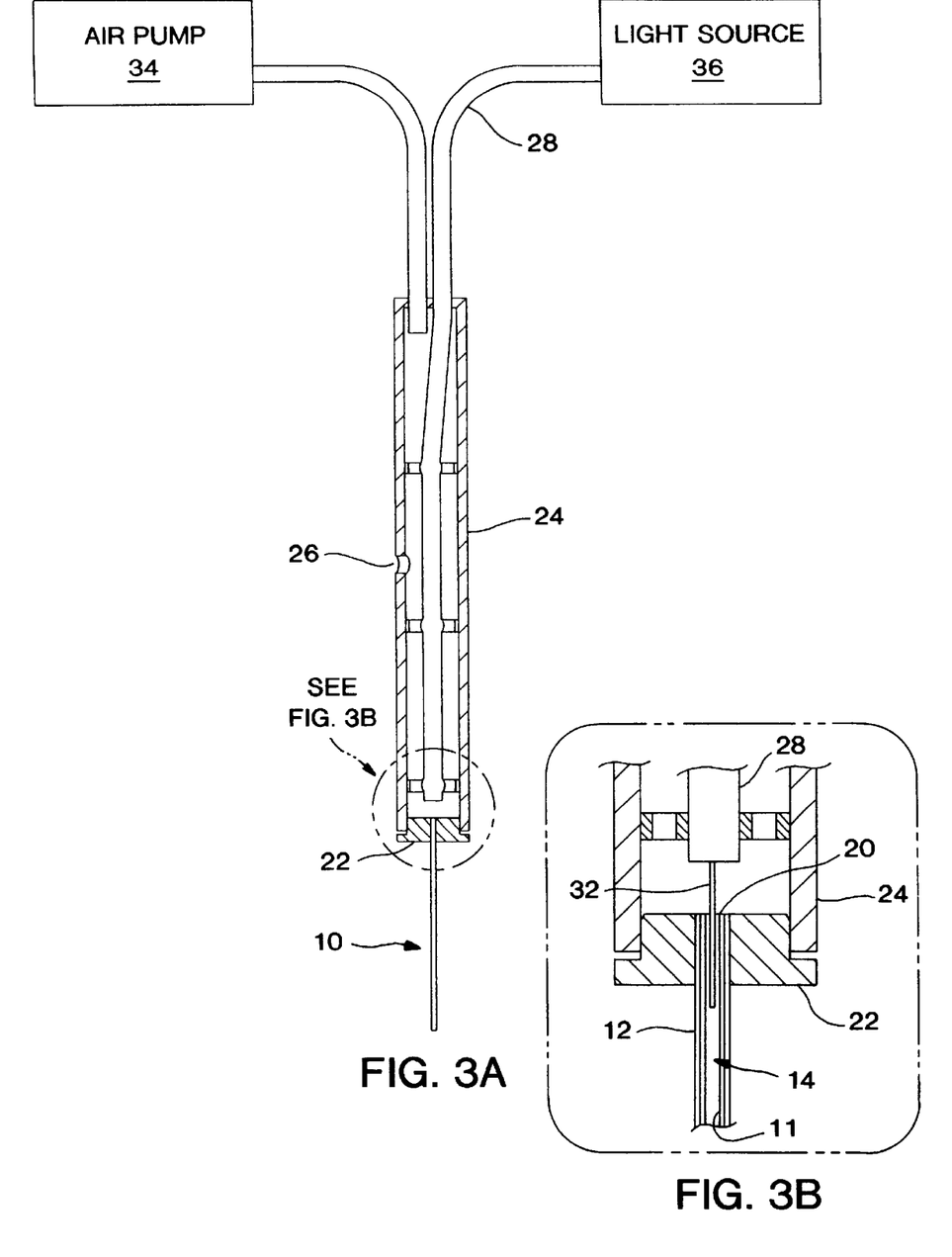
FIG. 3A is a view similar to FIG. 1 depicting a third embodiment of sampling apparatus in accordance with the invention.
FIG. 3B is an enlarged, partial view of the apparatus of FIG. 3A.

With reference to FIGS. 1–3, and particularly FIG. 3B, the present invention is founded upon the fabrication and use of a specially constructed micro-capillary sampling device. This device, hereinafter referred to as a "cell" and indicated generally at 10, comprises a capillary tube 11 fabricated from an optically transparent material capable of exerting an appropriate surface force upon liquids. The capillary tube 11 is preferably comprised of glass, fused silica or quartz. Capillary tube 11, as depicted in FIG. 3B, is coated on its exterior wall with a material 12 having a refractive index which is less than that of water, i.e., less than 1.33. Such a coated, optically transparent capillary tube, when its core region 14 is filled with an aqueous or other liquid which will transmit light, will function as a waveguide. For a further discussion of liquid core optical waveguides, reference may be had to U.S. Pat. No. 5,570,447. Reference may also be had to "A cylindrical liquid-core waveguide", P. Dress et al, Applied Phys., B 63, 12–19 (1996) and "A fiber-optic pipette for rapid long-pathlength capillary spectroscopy", C. M. Stellman et al, Sensors and Actuators, B 46, 56–60 (1998).

As represented in FIG. 1, the cell 10 is self-filling, as a consequence of capillary action, when its tip, i.e., its proximal end, 16 is immersed in a sample fluid droplet such as indicated at 18 and the pressure at its distal end 20 is the same as the ambient pressure acting on the surface of the droplet. Fluid from droplet 18 will rise into a previously emptied tube until it reaches the distal end 20 thereof. The surface tension of the sample liquid will prevent its overflow into a holder 24 from which cell 10 is supported. In summary, the cell 10 will fill spontaneously. By insuring that all fluid is ejected from cell 10 after each sample has been collected and analyzed, fluid samples may be accurately and repetitively acquired using a cell 10 of the invention. As will be described below, such collecting and measuring can be performed in a very short time. Furthermore, as will be described below, the sample collection and the subsequent measurement can be performed in a few seconds, the time being limited only by the time required to position the proximal end of the cell 10 in the liquid to be sampled and then repositioning end 16 of cell 10 in a detecting device or position.

To continue the above discussion, the length and inner diameter of a capillary tube 11 of a cell 10 precisely defines the volume of the sampling cell and thus defines the volume of the sample. Restated, each and every sample which is obtained by employing the invention in the manner depicted in FIG. 1 is precisely equal to the volume of the bore of cell 10. For example, a capillary tube with a length of one centimeter and a bore diameter of 25 micrometers has an internal volume of 4.9 nanoliters. Thus, in the practice of the present invention, a capillary tube may be cut to an exact length and will thus become an accurate and reproducible fluid volume collector.

Figure 4:
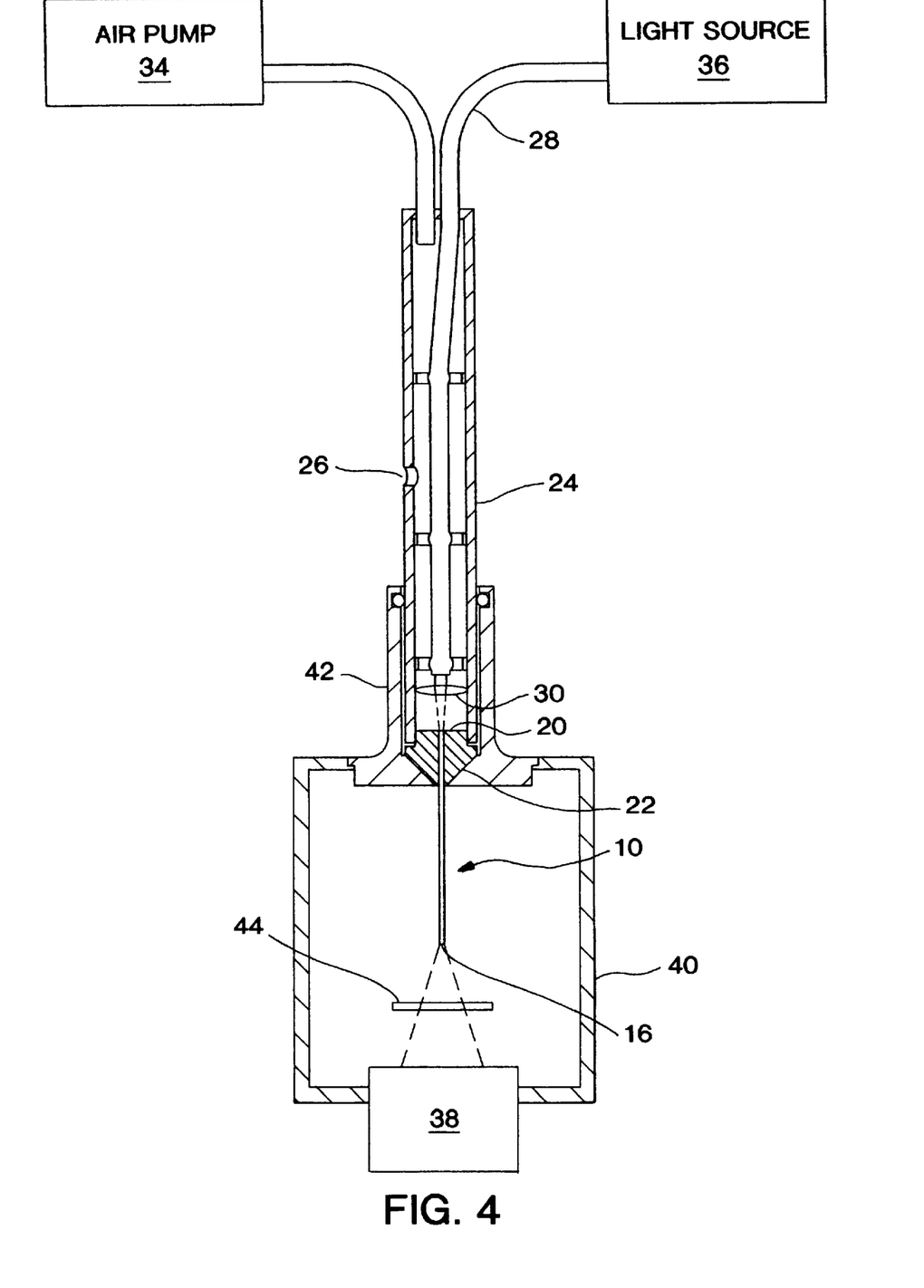
FIG. 4 is a schematic, side-elevational view, partially in cross-section, depicting the sampling apparatus of FIG. 2 as employed to implement a first measurement technique.
Figure 5:
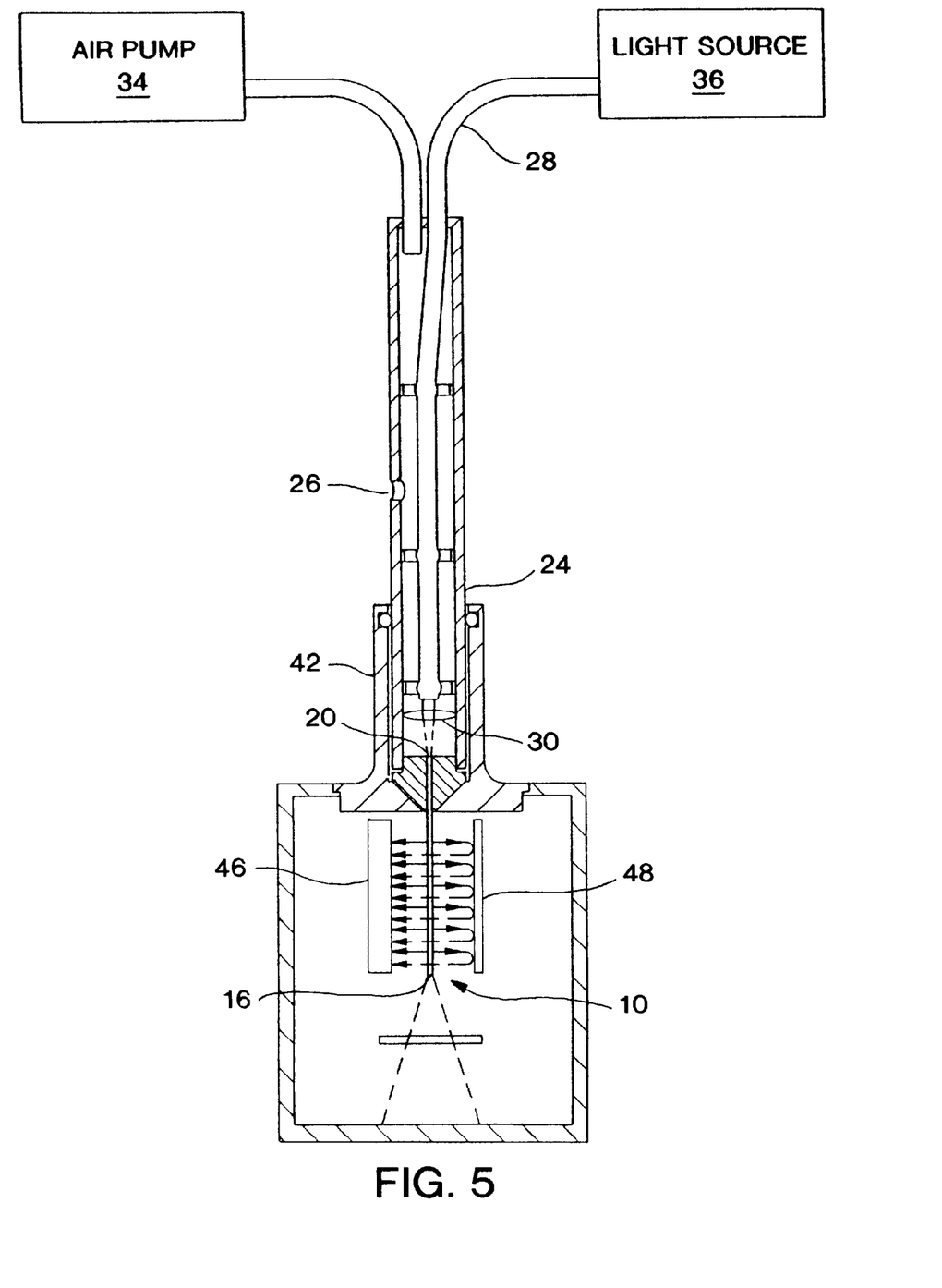
FIG. 5 is a view similar to FIG. 4 but depicting the implementation of a second type of measurement technique.
Figure 6:
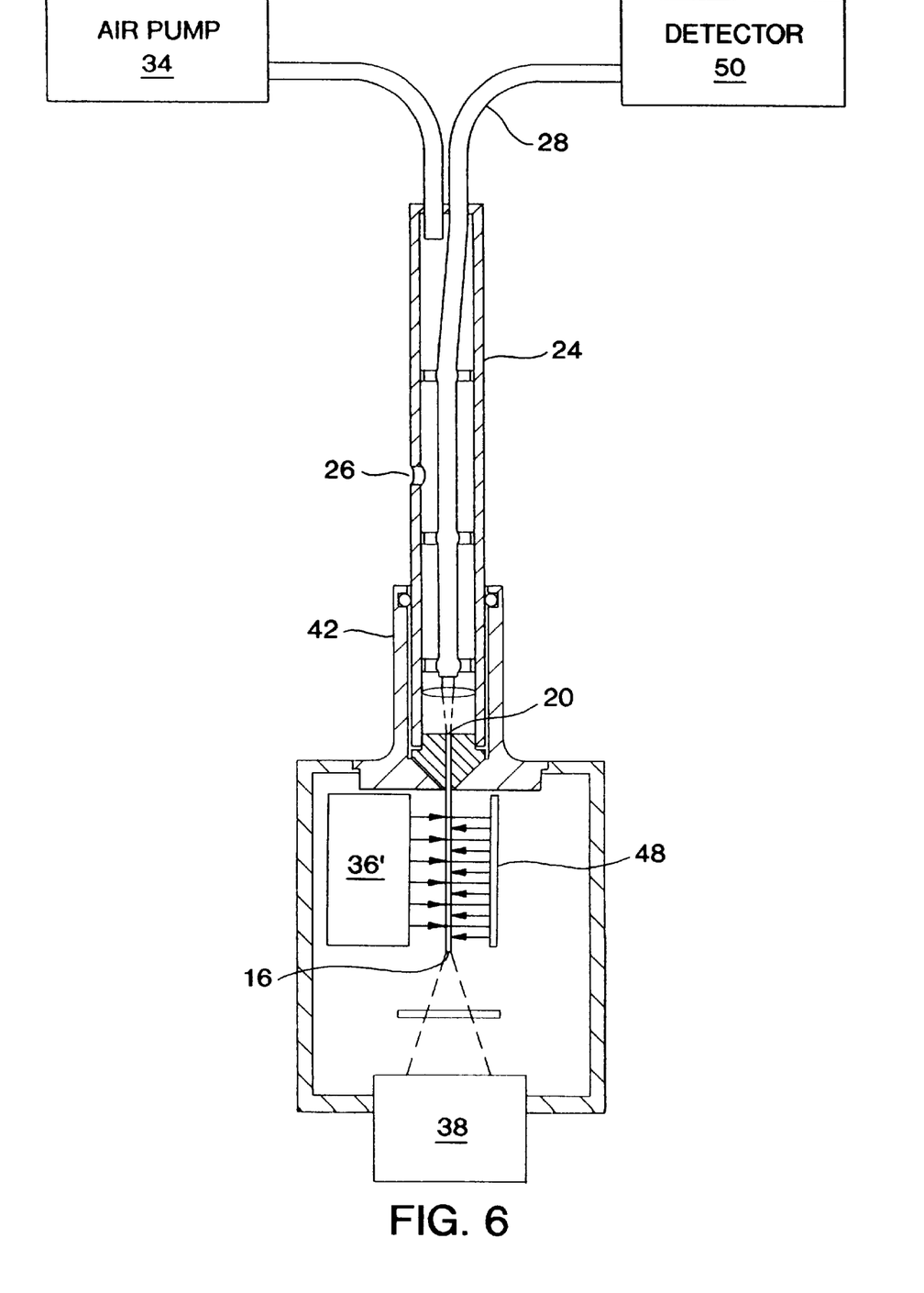
FIG. 6 is a view similar to FIG. 5 depicting an alternative manner of implementing the measurement technique of FIG. 5.

A first end of the cell 10 is fitted into a plastic or metal hub 22. The hub 22 may, as depicted in FIGS. 4–6, at least in part be conically shaped so as to facilitate mating with an analysis instrument. The hub 22, with the cell 10, is inserted in the first end of a tubular holder 24 which may be comprised of metal, plastic or any other suitable material. The interface between hub 22 and holder 24 preferably establishes an air tight seal whereby, as will be discussed below, the interior of holder 24 may be selectively pressurized. Holder 24 is, in the disclosed embodiment, provided with an air vent port 26 whereby the ambient atmospheric pressure may be established within the holder when a sample is to be collected.

In order to permit an optical measurement to be performed upon a sample disposed in cell 10, the sample must be illuminated by measurement light. The measurement light may be launched into the core region of the optical waveguide at an angle which is within the acceptance angle of the waveguide. Also, light which results from the illumination of a fluid in the core region of the cell by measurement light must be collected and analyzed. In accordance with the disclosed embodiments of the invention, measurement light may either be delivered to or received from cell 10 by means of a solid optical fiber which extends into and along tubular holder 24. Referring to FIG. 1, an end of optical fiber 28 is juxtaposed to the top or distal end 20 of cell 10, and the optical fiber 28 and cell 10 are supported so as to be coaxial. In the embodiment of FIG. 2, a lens 30 is positioned between end 20 of cell 10 and the facing end of optical fiber 28 so as to focus light emitted from the end of optical fiber 28 on the top 20 of cell 10. Alternatively, lens 30 will function to focus the image of end 20 of cell 10 onto the end of optical fiber 28. In the FIG. 3 embodiment, a small fiber optic 32, which may, for example, have a diameter which is in the range of 50 micrometers, is inserted into the core region 14 of cell 10 at the top 20 thereof, such insertion being, for example, to a depth of 2 or 3 mm.

In the disclosed embodiments of the invention, positive air pressure from a continuously running pump 34 is applied to the interior of tubular holder 24. While acquiring a fluid sample, and during subsequent illumination of the sample with measurement light, air from pump 34 is allowed to escape via the port 26. Consequently, except when it is desired to expel a sample from the core region of cell 10, there is virtually no excess air pressure at distal end 20 of capillary tube 11 i.e., the pressure in the interior of holder 24 will be equalized to the ambient atmospheric pressure by air flow through port 26. In order to expel a fluid sample from cell 10, the vent port 26 is closed whereupon the pressure within tubular holder 24 will increase above atmospheric pressure and the sample will be expelled via the tip 16 of cell 10. Alternatively, rather than employing the vent port 26 to control the internal pressure of holder 24, the pump 34 could be controlled, i.e., turned on and off. Also, means other than an air pump can be employed for pressurizing the interior of the tubular holder 24.

As noted above, utility of the present invention as part of an optical measurement system is optimized by providing the coating 12 on the exterior of a glass, silica or quartz capillary tube 11. The preferred coating is a copolymer of 2,2 bis trifuoromethyl-4,5 difluoro-1,3 dioxole (PDD) with tetrafluoroethylene (TFE). This material is sold commercially as "Teflon AF" and is a transparent amorphous polymer. The use of a polymer clad capillary tube is preferred because the coating on such a tube imparts greater physical strength to the capillary, whereupon the capillary exhibits a greater tolerance to bending without breaking, while also resisting wetting of the outside of the cell 10. The self-filling characteristic of sampling devices in accordance with the present invention dictates that the interior walls of the micro-capillary be naturally hydrophilic. Accordingly, the combination of self-filling capability and the ability to function as a liquid core optical waveguide requires that the capillary be comprised of a material such as glass, silica and quartz that is "wettable" while desirable physical characteristic and enhanced waveguiding action are achieved by the provision of an exterior polymer coating having a refractive index of less than 1.33.

In all of FIGS. 1–5, the fluid sample, i.e., the liquid core present in the cell 10, is axially illuminated with measurement light provided by an external source 36 coupled to the distal end of optical fiber 28 which is located remotely from the end of the optical fiber which is juxtapositioned to the top 20 of cell 10. Light source 36 may be any of a variety of light generators such as lasers, light emitting diodes, halogen lamps and other light sources well-known in the art.

FIG. 4 depicts the use of the sampling device of FIG. 2 to perform either an absorbance or fluorescence measurement on a sample located in cell 10. The filled cell is exposed to measurement light provided by source 36. In its passage through the capillary, the measurement light is attenuated by the absorptive properties of the sample fluid in the core region. A light detector 38, which may be a photocell, photomultiplier, spectrometer or other appropriate photo-detection means, is housed in an enclosure 40 and positioned such that light which has traveled the length of the optical waveguide 10 and exited the tip 16 thereof will impinge on detector 38. The employment of enclosure 40 enhances collection efficiency by shielding the cell 10 and detector 38 from ambient light. Enclosure 40 is provided with a suitably shaped tubular receiver 42 which will guide the end of tubular holder 24, and particularly the hub 22, into the proper position. When detecting fluorescent light which is emitted as a result of excitation of the sample by the measurement light, a light filter 44 may, if necessary, be placed in the path of the light exiting tip 1 6 to suppress interfering light from impinging on the detector 38. As will be understood by those skilled in the art, neither the enclosure 40 or filter 44 are essential for practice of the invention.

The embodiment depicted in FIG. 4 may also be employed to obtain either fluorescence or Raman spectra of analytes in the sample fluid in the core region of cell 10. In order to obtain Raman spectra, the measurement light is preferably coherent and of high intensity, i.e., source 36 will desirably be a laser. In such case, the detector 38 will be a high resolution spectrometer, and the filter 44 will be a narrow wavelength band light blocking filter centered at the wavelength of the measurement light. This will substantially prevent measurement light from entering the spectrometer while Raman scattered light will pass through the filter and be detected. It should be noted that, since an optical fiber will itself contribute to Raman scattering and thus have a deleterious effect on the results of the analysis, it is possible to enhance the accuracy of the results obtained when using the FIG. 4 embodiment for Raman spectroscopy by locating the source of coherent measurement light within the tubular holder 24 whereby the laser light will be focused directly at the top 20 of cell 10.

FIG. 5 represents the sampling device of FIG. 2 as employed to measure sample fluid fluorescence and other scattering light processes such as Raman spectra, Rayleigh scattering and chemiluminescence. Many analytes will fluoresce, or can be made to do so by the addition of appropriate fluorescent dyes, when excited by a light of an appropriate wavelength. Such light causes the excitation of fluorescent molecules within the sample with consequent light emission at another wavelength, the wavelength of the fluorescent light typically being longer than that of the excitation light. Fluorescence is a particularly sensitive measure of dissolved fluorescent analytes. In the FIG. 5 embodiment, the excitation of the sample is achieved in the manner discussed above, i.e., the excitation light is axially directed via the optical fiber 28 into the top 20 of the cell 10. Fluorescent light with an intensity dependent on the concentration of dissolved fluorophores in the cell is emitted and scattered in all directions. Fluorescent light which is generated will thus be emitted from the tip 16 of cell 10 and may be detected as discussed above, i.e., filtered to suppress excitation wavelengths and collected by a photo-detector located in registration with the cell axis. In the FIG. 5 embodiment, however, a fluorescent light detector 46 is located parallel to the axis of cell 10 and receives fluorescent light rays emitted generally transversely to the axis of the cell. For increased efficiency, a mirror 48 is appositely placed with respect to detector 46 to reflect additional fluorescent light toward the detector. The mirror 48 may, obviously, be either planar or curved to more effectively concentrate the reflected fluorescent light at detector 46. In most fluorescent detection schemes, excitation light filters are placed between the source of the fluorescent light and the detector(s) to filter out scattered excitation light which could otherwise be a large contributor to the light impinging upon the detector. The present invention has the important advantage that most of the excitation light will be confined by waveguide action to the liquid in the core region of the capillary and, therefore, will not significantly interfere with the detection of emitted fluorescent light by detector 46, even at low fluorescent light intensities. Thus, the present invention may be practiced so as to diminish the need to employ excitation light filtering. As noted above, the transverse light detection is not limited to measurement of fluorescence but also is suitable for detecting any other scattered light such as Raman spectra, Rayleigh scattering and chemiluminescence.

The embodiment of FIG. 6 differs from the above-described embodiments in that the measurement light source, indicated at 36', is located within enclosure 40. Measurement light from source 36' irradiates the sample transversely to the axis of cell 10. In the FIG. 6 embodiment, measurement light reflected from mirror 48 augments the excitation light directly impinging on the capillary. A portion of the fluorescent light produced in the fluid sample is confined to the interior of cell 10 by waveguide action and will propagate to both of ends 16 and 20. This fluorescent light can be collected by detector 38 and/or be transmitted, via optical fiber 28, to a second detector 50. As in the embodiment of FIG. 5, the action of the liquid core waveguide separates emitted fluorescent light from the excitation light and thus reduces or eliminates the need for excitation light filtering.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method for the performance of an analytical procedure on a test liquid, said method including the steps of:

selecting an open-ended tubular sampling member having a bore with a predetermined volume, the dimensions of the bore being chosen to insure spontaneous and complete filling thereof due to capillary action when an open first end of the sampling member is immersed in the test liquid, the sampling member bore being defined by a surface which is hydrophilic;

engaging the second end of the sampling member by the first end of a tubular holder, the sampling member being supported such that the bore thereof is open to the interior of the holder, the sampling member extending from the holder to the first end of the sampling member, the exterior of the sampling member adjacent the open second end thereof being sealed to the interior of the holder;

establishing atmospheric pressure in the interior of the holder;

inserting the first end of the sampling member in the test liquid whereby the test liquid will spontaneously flow into and fill the sampling member bore thus forming a sample of said predetermined volume;

transporting the sample in the sampling member to an analysis station for analysis by illumination with measurement light; and pressurizing the interior of the holder to eject the sample from the bore of the sampling member subsequent to illumination.

2. The method of claim 1 wherein the step of selecting comprises:

forming a liquid core optical waveguide, the waveguide comprising a transparent rigid capillary tube consisting of a hydrophilic material, the capillary tube having an external coating of a material with a refractive index of less than 1.33, the bore of the capillary tube comprising the core region of the waveguide.

3. The method of claim 2 further comprising:

illuminating the core region of the waveguide with measurement light prior to pressurization of the holder; and collecting and analyzing light resulting from the passage of the measurement light through the sample in the waveguide core region.

4. The method of claim 3 wherein the step of transporting comprises:

isolating the waveguide from ambient light to enhance the efficiency of the collection of light for analysis.

5. The method of claim 3 wherein the step of illuminating comprises:

delivering measurement light from a source through the holder to the second end of the waveguide, the majority of the delivered light being launched into the waveguide core region at the second end thereof and at an angle which is less than the acceptance angle of the waveguide.

6. The method of claim 5 wherein the step of transporting comprises:

mating the holder with a complementary shaped receiver of an analysis instrument, the receiver being on the exterior of an enclosure, the first end of the waveguide extending into the enclosure subsequent to mating, the enclosure enhancing the efficiency of the step of collecting by isolating the waveguide from ambient light.

7. The method of claim 3 wherein the step of illumination comprises:

directing the measurement light to the waveguide so as to illuminate the sample in a direction which is generally transverse to the axis of the waveguide.

8. The method of claim 4 wherein the step of illumination comprises:

directing the measurement light to the waveguide so as to illuminate the sample in a direction which is generally transverse to the axis of the waveguide.

9. The method of claim 3 wherein the step of collecting and analyzing comprises:

measuring the absorption of the measurement light by the sample in the waveguide core region.

10. The method of claim 3 wherein the step of collecting and analyzing comprises:

measuring the Raman spectra of the illuminated sample in the waveguide core region.

11. The method of claim 3 wherein the step of collecting and analyzing comprises:

measuring the fluorescent light emitted by the illuminated sample in the waveguide core region.

12. The method of claim 7 wherein the step of collecting and analyzing comprises:

measuring the fluorescent light emitted by the illuminated sample in the waveguide core region.

13. The method of claim 12 wherein the step of collecting and measuring further comprises:

collecting light emitted by the sample at the first end of the holder; and delivering the collected light through the holder to an analysis instrument.

14. Apparatus for use in the optical measurement of a liquid comprising:

a sampling member, said sampling member comprising a liquid core optical waveguide defined by a rigid capillary tube, said tube having a cylindrical bore of predetermined volume extending between first and second opposite open ends, said tube being comprised of a transparent material which is hydrophillic, the length and diameter of said bore being selected to insure complete filling thereof by capillary action when a first end of said tube is immersed in a liquid to be analyzed and the second end of said tube is at the ambient pressure of the space in which the liquid is situated whereby said liquid will form the liquid core of the waveguide;

a tubular holder having first and second oppositely disposed ends;

means supporting said second end of said capillary tube from said first end of said holder with said bore of said capillary tube in direct fluid communication with the interior of said holder, said supporting means establishing a substantially fluid-tight seal between the interior of said holder and the exterior of said capillary tube, said capillary tube extending from said supporting means to said first end of said capillary tube;

means for varying the pressure in the interior of said holder between said ambient pressure and a pressure greater than said ambient pressure to thereby selectively allow said capillary tube cylindrical bore to fill with liquid by capillary action or to expel liquid from said cylindrical bore; and means for conveying light through said holder between said first and second ends, said light conveying mean comprising a solid optical fiber having a first end juxtapositioned to said second end of said capillary tube.

15. The apparatus of claim 14 wherein said optical waveguide further comprises:

a coating on the exterior surface of said capillary tube, said coating being comprised of a material having an index of refraction which is less than 1.33.

16. The apparatus of claim 15 further comprising:

a source of measurement light; and means for collecting for analysis light resulting from a passage of measurement light through the waveguide liquid core.

17. The apparatus of claim 16 wherein said capillary tube, said holder and at least said first end of said solid optical fiber are coaxial and wherein said source of measurement light is optically coupled to said second end of said solid optical fiber whereby the measurement light from said source is launched into optical fiber at an angle which is within the acceptance angle of said waveguide.

18. The apparatus of claim 17 wherein said means for collecting comprises:

means defining an enclosure;

a receiver mounted on said enclosure defining means, said receiver including an opening through which said first end of said capillary tube may be inserted, said receiver mating with said supporting means; and a detector positioned within said enclosure for receiving light exiting said optical waveguide.

19. The apparatus of claim 16 further comprising a lens disposed between said first end of said optical fiber and said second end of said tube.

20. The apparatus of claim 14 wherein said supporting means is mounted on said coated capillary tube for movement with said waveguide relative to said receiver.

21. Apparatus for use in the optical measurement of a liquid comprising:

a sampling member, said sampling member comprising:

a liquid core optical waveguide comprising a rigid capillary tube, said tube having a cylindrical bore of predetermined volume extending between first and second opposite open ends, said bore forming the core region of said waveguide, said tube being comprised of a material which is hydrophilic, the length and diameter of said bore being selected to insure complete filling of said core region of said waveguide by capillary action when a first end of said tube is immersed in a liquid to be analyzed and the second end of said tube is at the ambient pressure of the space in which the liquid is situated whereby said liquid will form the liquid core of the waveguide; and a coating on the exterior surface of said capillary tube, said coating being comprised of a material having an index of refraction which is less than 1.33;

a tubular holder having first and second oppositely disposed ends;

means supporting said second end of said coated capillary tube from said first end of said tubular holder, said supporting means establishing direct fluid communication between said cylindrical bore of said capillary tube and the interior of said holder, said supporting means further establishing a substantially fluid-tight seal between the interior of said holder and the exterior of said capillary tube, said capillary tube extending from said supporting means to said first end of said capillary tube;

means for varying the pressure in the interior of said holder between said ambient pressure and a pressure greater than said ambient pressure to thereby selectively allow said capillary tube bore to fill with liquid by capillary action or to expel liquid from said cylindrical bore;

means defining an enclosure;

a receiver mounted on said enclosure defining means, said receiver including an opening through which said first end of said capillary tube may be inserted into said enclosure, said receiver mating with said supporting means;

means for causing liquid in the core region of said waveguide to be illuminated, said illumination causing means including a source of measurement light; and means for collecting for analysis light resulting from the passage of measurement light through the waveguide liquid core.

22. The apparatus of claim 21 wherein said illumination causing means further includes a solid optical fiber which extends through said tubular holder, a first end of said solid optical fiber being juxtapositioned to said second end of said capillary tube, wherein said source of measurement light is optically coupled to said second end of said solid optical fiber and wherein said means for collecting is in said enclosure.

23. The apparatus of claim 21 wherein said source of measurement light is located within said enclosure.

24. The apparatus of claim 23 wherein said source of measurement light provides light comprising rays which are directed transversely with respect to the axis of said cylindrical bore of said tube.

* * * * *